US011301997B2

(12) United States Patent
Majeed et al.

(10) Patent No.: US 11,301,997 B2
(45) Date of Patent: Apr. 12, 2022

(54) IMAGE REGISTRATION AND PRINCIPAL COMPONENT ANALYSIS BASED MULTI-BASELINE PHASE CORRECTION METHOD FOR PROTON RESONANCE FREQUENCY THERMOMETRY

(71) Applicants: Siemens Healthcare GmbH, Erlangen (DE); THE UNITED STATES OF AMERICA, AS REPRESENTED BY THE SECRETARY, DEPARTMENT OF HEALTH AND HUMAN SERVICES, Bethesda, MD (US)

(72) Inventors: Waqas Majeed, Ellicott City, MD (US); Himanshu Bhat, Newton, MA (US); Rainer Schneider, Erlangen (DE); Adrienne Campbell, Bethesda, MD (US)

(73) Assignees: Siemens Healthcare GmbH, Erlangen (DE); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 204 days.

(21) Appl. No.: 16/849,313

(22) Filed: Apr. 15, 2020

(65) Prior Publication Data
US 2020/0342591 A1 Oct. 29, 2020

Related U.S. Application Data

(60) Provisional application No. 62/840,006, filed on Apr. 29, 2019.

(51) Int. Cl.
G06K 9/00 (2006.01)
G06T 7/00 (2017.01)
(Continued)

(52) U.S. Cl.
CPC ............ G06T 7/0012 (2013.01); A61B 5/015 (2013.01); G06T 7/215 (2017.01); G06T 7/38 (2017.01);
(Continued)

(58) Field of Classification Search
CPC . A61B 5/015; A61B 2090/374; A61B 5/0036; A61B 18/20; G01R 33/56509;
(Continued)

(56) References Cited

U.S. PATENT DOCUMENTS

| 2008/0287773 | A1* | 11/2008 | Harvey | .............. | G01R 33/4804 |
| | | | | | 600/412 |
| 2011/0109309 | A1* | 5/2011 | Levy | ...................... | A61B 5/055 |
| | | | | | 324/309 |

(Continued)

OTHER PUBLICATIONS

Donoho, David L., and Matan Gavish. "The optimal hard threshold for singular values is 4/ √3." arXiv preprint arXiv:1305.5870 4(2013).

(Continued)

Primary Examiner — Shervin K Nakhjavan

(57) ABSTRACT

A method for phase correction in proton resonance frequency (PRF) thermometry application includes acquiring a series of magnetic resonance (MR) images comprising a first MR image and plurality of subsequent MR images depicting an anatomical area of interest. The MR images are acquired while tissue in the anatomical area of interest is undergoing a temperature change. Each subsequent MR image is registered to the first MR image to yield a plurality of registered images. A plurality of basis images are computed from the registered images using Principal Component Analysis (PCA). The basis images are used to remove motion-related phase changes from a second series of MR images, thereby yielding a motion corrected second series of MR images. One or more temperature difference maps are generated that (Continued)

depict a relative temperature change for the tissue in the anatomical area of interest based on the motion corrected second series.

18 Claims, 8 Drawing Sheets
(3 of 8 Drawing Sheet(s) Filed in Color)

(51) Int. Cl.
*G06T 7/38* (2017.01)
*G06T 7/215* (2017.01)
*A61B 5/01* (2006.01)

(52) U.S. Cl.
CPC .............. *G06T 2207/10088* (2013.01); *G06T 2207/20182* (2013.01); *G06T 2207/20201* (2013.01)

(58) Field of Classification Search
CPC ....... G06T 7/0012; G06T 7/38; G06T 7/0016; G06T 2207/10088; G06T 2207/20182; G06T 2207/20224
See application file for complete search history.

(56) References Cited

U.S. PATENT DOCUMENTS

| | | | | |
|---|---|---|---|---|
| 2011/0306870 | A1* | 12/2011 | Kuhn | A61N 1/406 600/411 |
| 2015/0087963 | A1* | 3/2015 | Tyc | A61B 18/22 600/411 |
| 2015/0169836 | A1* | 6/2015 | Vahala | A61N 7/02 600/411 |
| 2015/0227702 | A1* | 8/2015 | Krishna | A61B 5/7257 705/2 |
| 2021/0093897 | A1* | 4/2021 | Zadicario | A61B 34/20 |

OTHER PUBLICATIONS

Rieke, Viola, and Kim Butts Pauly. "MR thermometry." Journal of Magnetic Resonance Imaging: An Official Journal of the International Society for Magnetic Resonance in Medicine 27.2 (2008): 376-390.

Roujol, Sébastien, et al. "Real-time MR-thermometry and dosimetry for interventional guidance on abdominal organs." Magnetic Resonance in Medicine: An Official Journal of the International Society for Magnetic Resonance in Medicine 63.4 (2010): 1080-1087.

Odéen, Henrik, et al. "Sampling strategies for subsampled segmented EPI PRF thermometry in MR guided high Intensity focused ultrasound." Medical physics 41.9 (2014): 092301.

Foupin, Solenn, et al. "Feasibility of real-time MR thermal dose mapping for predicting radiofrequency ablation outcome in the myocardium in vivo." Journal of Cardiovascular Magnetic Resonance 19.1 (2017): 1-12.

Rieke, Viola, et al. "Comparison of temperature processing methods for monitoring focused ultrasound ablation in the brain." Journal of Magnetic Resonance Imaging 38.6 (2013): 1462-1471.

* cited by examiner

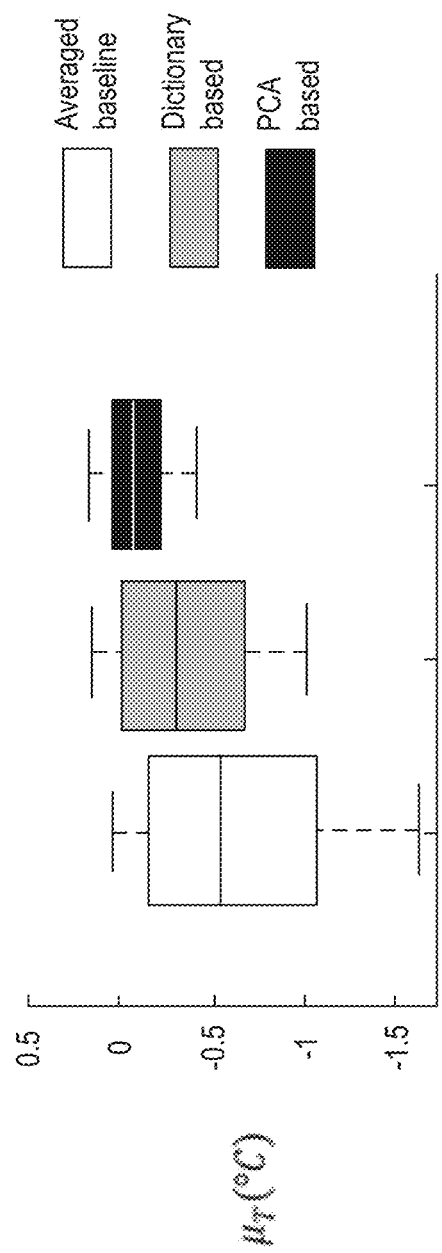

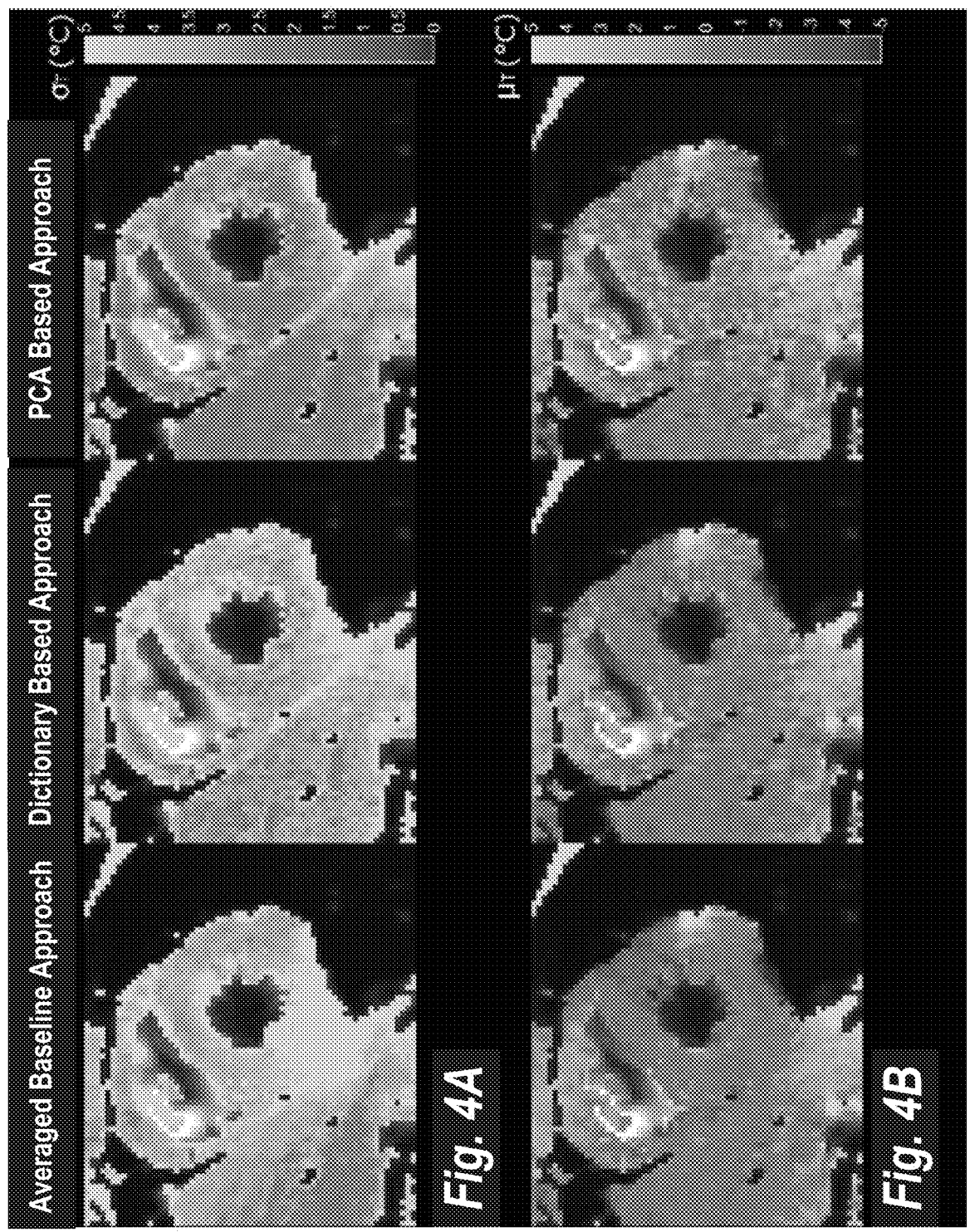

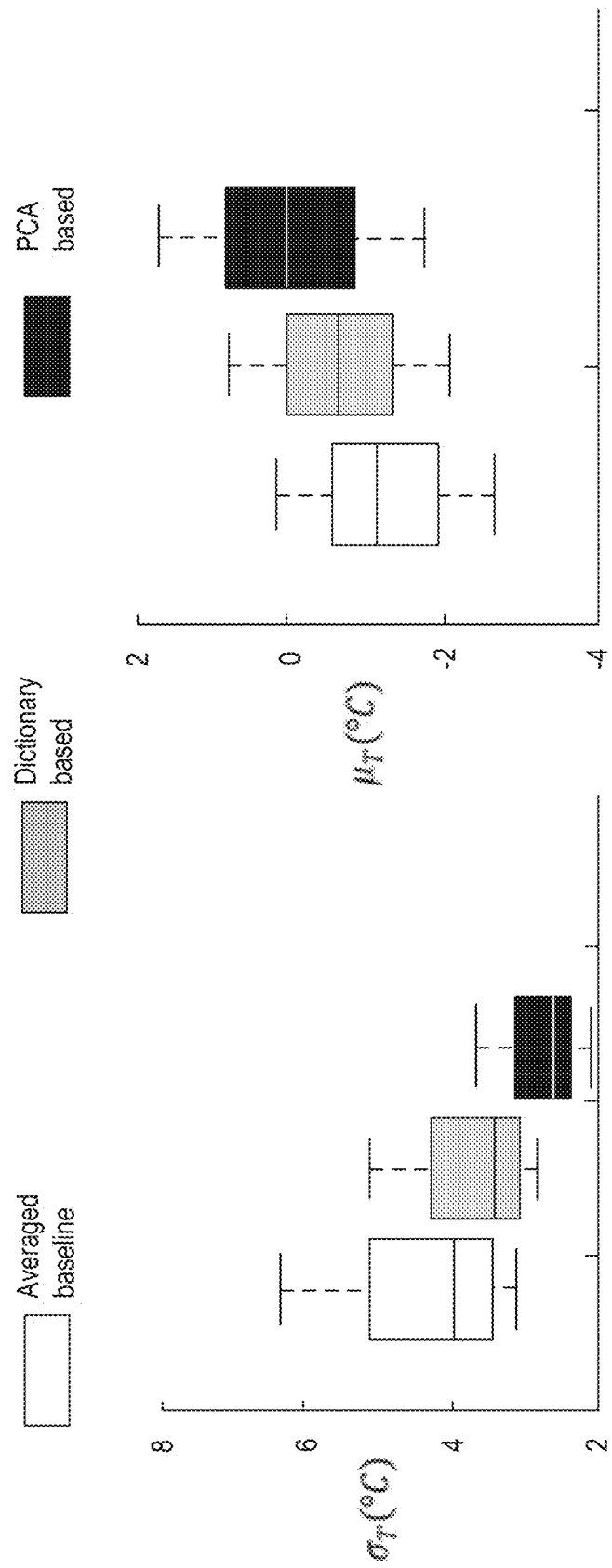

IMAGE REGISTRATION AND PRINCIPAL COMPONENT ANALYSIS BASED MULTI-BASELINE PHASE CORRECTION METHOD FOR PROTON RESONANCE FREQUENCY THERMOMETRY

TECHNICAL FIELD

The present invention relates generally to thermal therapy procedures, and more particularly to a multi-baseline phase correction method for proton resonance frequency (PRF) thermometry method that uses principal component analysis. The techniques described herein may be used, for example, to increase the accuracy of PRF thermometry in or near moving organs, and hence result in improved clinical outcome.

BACKGROUND

Proton Resonance Frequency (PRF) thermometry is a widely used Magnetic Resonance Imaging (MRI) based technique to monitor changes in tissue temperature in response to thermal therapy. The use of PRF thermometry with thermal therapy procedures (e.g., High Intensity Focused Ultrasound (HIFU) and Laser based heating) is indispensable to ensure delivery of desired thermal dose to the target tissue, and to minimize unintended damage to the normal tissue. PRF thermometry relies on phase difference between the acquired images, and therefore motion related $B_0$ changes in organs of interest and background adversely affect the accuracy of temperature difference estimates, even when registration-based motion correction is performed to correct for displacements

SUMMARY

Embodiments of the present invention address and overcome one or more of the above shortcomings and drawbacks, by providing methods, systems, and apparatuses related to combination of registration-based motion correction with a multi-baseline phase correction method for PRF thermometry method that uses principal component analysis. An improvement in PRF thermometry technique will play a vital role in more widespread clinical adoption of thermal therapy. The method described herein will add to the tools available to overcome the challenges of PRF thermometry, especially in moving organs.

According to some embodiments, a method for phase correction in proton resonance frequency (PRF) thermometry application includes acquiring a series of magnetic resonance (MR) images comprising a first MR image and plurality of subsequent MR images depicting an anatomical area of interest. The MR images are acquired while tissue in the anatomical area of interest is undergoing a temperature change. Each subsequent MR image is registered to the first MR image to yield a plurality of registered images. A plurality of basis images are computed from the registered images using Principal Component Analysis (PCA). The basis images are used to remove motion-related phase changes from a second series of MR images, thereby yielding a motion corrected second series of MR images. One or more temperature difference maps are generated that depict a relative temperature change for the tissue in the anatomical area of interest based on the motion corrected second series.

In other embodiments, an article of manufacture for phase correction in PRF thermometry applications comprises a non-transitory, tangible computer-readable medium holding computer-executable instructions for performing a method that includes receiving MR images comprising a first MR image and plurality of subsequent MR images depicting an anatomical area of interest. The MR images are acquired while tissue in the anatomical area of interest is undergoing a temperature change. As with the method described above, each subsequent MR image to the first MR image to yield a plurality of registered images and basis images are computed from the registered images using PCA. The basis images are used to remove motion-related phase changes from a second series of MR images. One or more temperature difference maps are generated that depict a relative temperature change for the tissue in the anatomical area of interest based on the motion corrected second series.

According to another aspect of the present invention, a system for phase correction in PRF thermometry applications includes a plurality of RF coils, one or more displays, and one or more computers. The RF coils are configured to acquire a series of MR images comprising a first MR image and plurality of subsequent MR images depicting an anatomical area of interest. The MR images are acquired while tissue in the anatomical area of interest is undergoing a temperature change. The computers are connected to the RF coils and configured to register each subsequent MR image to the first MR image to yield a plurality of registered images. The computers also compute a plurality of basis images from the registered images using PCA. These basis images are used to remove motion-related phase changes from a second series of MR images, thereby yielding a motion corrected second series of MR images. Temperature difference maps are generated for presentation on the display. The temperature difference maps depict a relative temperature change for the tissue in the anatomical area of interest based on the motion corrected second series.

Additional features and advantages of the invention will be made apparent from the following detailed description of illustrative embodiments that proceeds with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures:

FIG. 3A shows temporal mean maps of an estimated temperature difference series, comparing three different baseline removal schemes;

FIG. 3B shows box plots corresponding to the temporal mean of the estimated temperature difference series over an ROI drawn in the frontal cortex, as shown in FIG. 3A (row 1, column 2);

FIG. 4A standard deviation maps of an estimated temperature difference series for a cardiac thermometry dataset, comparing three different baseline removal schemes;

FIG. 4B shows temporal mean maps of an estimated temperature difference series for a cardiac thermometry dataset, comparing three different baseline removal schemes;

FIG. 4C shows box plots corresponding to the standard deviation of the estimated temperature difference series shown in FIG. 4A over an ROI covering the left ventricle;

FIG. 4D shows box plots corresponding to the temporal mean of the estimated temperature difference series shown in FIG. 4B over an ROI covering the left ventricle.

DETAILED DESCRIPTION

The present disclosure describes systems and methods for performing thermal therapy procedures. The use of Proton Resonance Frequency (PRF) based thermometry with thermal therapy procedures is indispensable. Variation in background phase due to motion related changes in $B_0$ is a major source of inaccuracy in PRF thermometry. The techniques described herein disclose combination of registration-based motion correction with a Principal Component Analysis (PCA) based multi-baseline phase correction approach. Examples are provided below that compare this approach with two existing methods using in-vivo human brain and heart data, and demonstrate significant reduction in bias as well as variance of temperature difference estimates. The PCA approach described herein may increase the accuracy of PRF thermometry in or near moving organs, and hence result in improved clinical outcomes.

Figure 1:
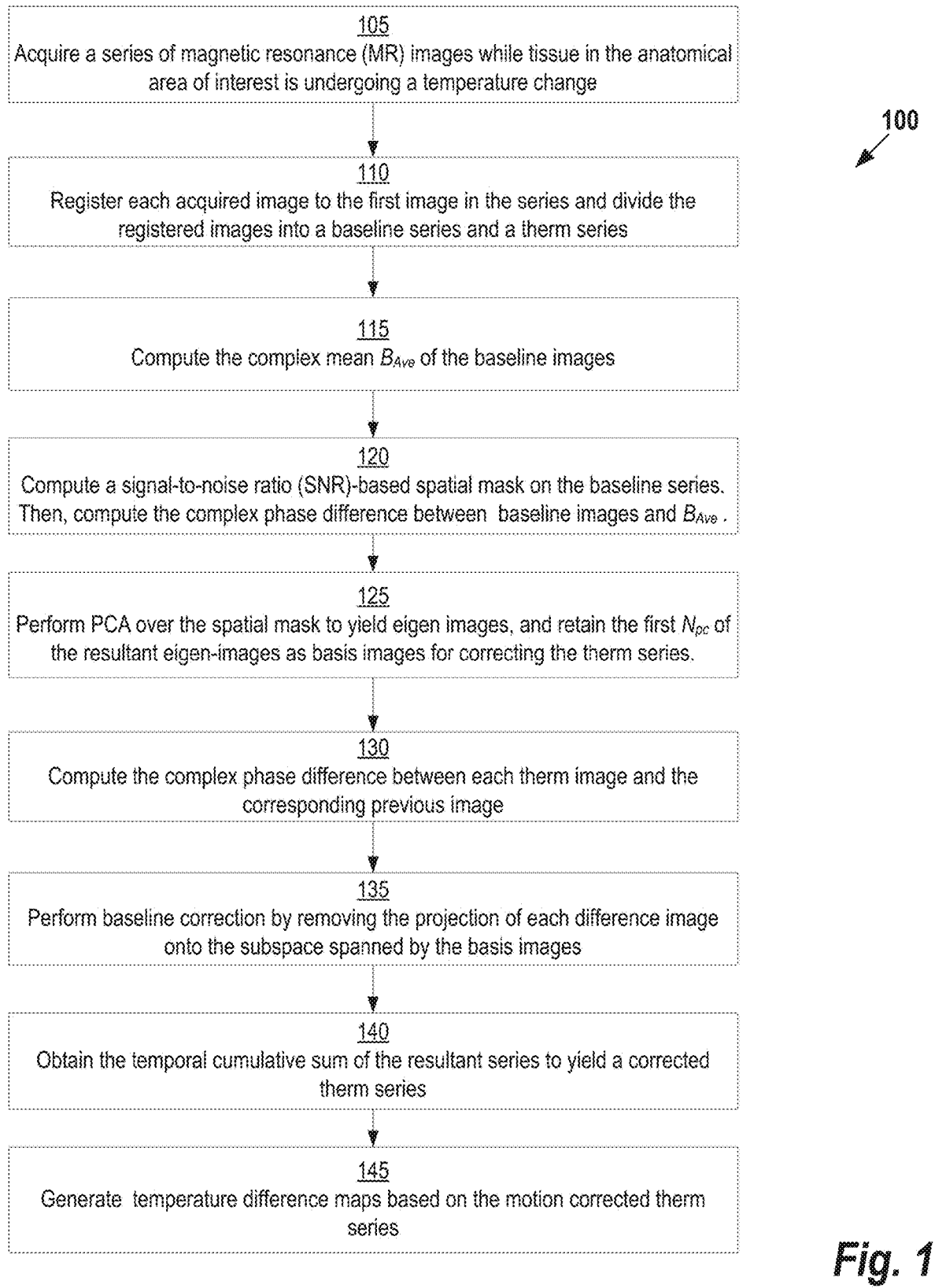
FIG. 1 shows an example method for correct motion related $B_0$ changes in PRF thermometry, according to some embodiments.

FIG. 1 shows an example method for correct motion related $B_0$ changes in PRF thermometry, according to some embodiments. Starting at step 105, a plurality of images are acquired from an MRI system using a gradient-recalled echo (GRE) sequence such as a 3D segmented Echo-planar imaging (EPI) sequence. One example of an MRI system is shown below with reference to FIG. 5. Various parameters may be used in implementing the GRE sequence. For example, in one embodiment, the parameters are as follows: repetition time (TR) 45 ms, echo time (TE) 23 ms, 1.25× 2.5×2.5 mm resolution, 192×96×12 matrix, segmented echo planar imaging (EPI) readout with EPI factor 9, 100 repetitions. For cardiac applications, navigated, single shot EPI images may be acquired at step 105. Example parameters for performing such an acquisition include one short axis slice, 2×2×4 mm resolution, GeneRalized Autocalibrating Partial Parallel Acquisition (GRAPPA) factor 2, saturation slabs parallel to the slice for blood suppression, 100 repetitions.

Next, at step 110, a pre-processing step is performed. During this step, each image acquired at step 105 is registered to the first image in the series. $N_B$ images of the series are designated as baseline images (also referred to herein as the "baseline series"). The baseline series are assumed to be acquired before heating of the tissue begins. The remaining images acquired at step 105 (referred to herein as the "therm series") are assumed to be acquired during heating. For example, if $N_B=20$, no heating will occur during first 20 images. Images 21 onward are part of "therm" series, even though the heating may start at Image 30. As explained in further detail below, the therm series may be used to compute temperature difference maps. The value of $N_B$ is a user-specified value. $N_B$ is based on the duration that captures the typical range of physiological and motion related variation. The exact value of $N_B$ may be optimized for each application based on experimentation.

Continuing with reference to FIG. 1, at steps 115-125, background phase information is removed is calculated using a Principal Component Analysis (PCA) based approach. Briefly, PCA is unsupervised statistical method to reduce the dimensionality of a large data set. In the context of image processing PCA may be applied to reduce a large dataset of images into a set of orthogonal basis images, sometimes referred to as "eigen images." These basis images can be linearly combined to form any image in the dataset.

At steps 115-125 basis images are computed. First, the complex mean of the baseline images (designed herein as $B_{Ave}$) is obtained. As is generally understood in the art, magnetic resonance images are reconstructed by applying Fourier transformations to complex-valued k-space data acquired in the frequency domain. The Fourier transformation results in complex-valued image data (i.e., each image includes real and imaginary data). The complex mean is computed by averaging over the baseline images using the real and imaginary information of each image. Next, at step 120, a signal-to-noise ratio (SNR)-based spatial mask is computed on the baseline series. Then, the complex phase difference between baseline images and $B_{Ave}$ is computed. Next, at step 125, PCA is performed on the phase difference images over the spatial mask to yield a plurality of eigen images. The first $N_{pc}$ of the resultant eigen-images are retained as basis images for correcting the therm series.

The value of $N_{pc}$ can be determined using a variety of model selection approaches for PCA. For example, in some embodiments, $N_{pc}$ is selected to capture a particular percentage of the total variance. In other embodiments, $N_{pc}$ may be selected using the thresholding technique set forth in M. Gavish and D. L. Donoho, "The Optimal Hard Threshold for Singular Values is $4/\sqrt{3}$" in *IEEE Transactions on Information Theory*, vol. 60, no. 8, pp. 5040-5053, August 2014. In other embodiments, $N_{pc}$ is selected based on Akaike's formation criterion or a minimum description-length criterion.

Steps 130-140 remove the baseline phase from the therm series, thereby removing motion-related $B_0$ changes. At step 130, the complex phase difference is computed between each therm image and the corresponding previous image. $B_{Ave}$ is used as the image previous to the first therm image. Next, at step 135, baseline correction is performed by removing the projection of each phase difference image onto the subspace spanned by the basis images. This projection may be obtained, for example, by 1) normalizing the basis images to unit norm over the spatial mask, 2) computing inner products between the phase difference image and basis images over the spatial mask, and 3) adding the bases images after weighting them by the corresponding inner-products. The resultant series contains phase difference between adjacent acquisitions with baseline phase removed. Then, at step 140, the temporal cumulative sum of the resultant series is obtained to compute motion corrected phase difference series relative to the first acquisition, also referred to as "motion corrected therm series".

Finally, at step 145 one or more temperature difference maps are generated that depict temperature change relative to the baseline series for the tissue in the anatomical area of interest based on the motion corrected therm series. The change in phase is used to estimate the relative temperature change ΔT is given by:

$$\Delta T = \frac{\Delta \phi}{\gamma \alpha B_0 TE}$$

where α=−0.001 ppm/° C. is the PRF change coefficient for aqueous tissue, γ is the gyromagnetic ratio, $B_0$ is the main magnetic field, TE is the echo time, and Δφ is the phase difference before and after heating as determined in step 140.

Although the implementation shown in FIG. 1 utilizes an offline implementation, the general method can readily be adopted to real-time thermometry. For example, assume that $N_B$ is pre-selected. Image acquisition is started and each image is registered to the first image immediately after acquisition. The first $N_B$ images are used as the baseline and steps 115-125 are performed. Every image acquired after the $N_B$-th image are assigned to the therm series. Steps 130-145 are performed to compute temperature difference between the therm series and the baseline series. Image registration based motion correction can also be combined with other PCA-based approaches, such as PCA performed on complex baseline series.

As a proof of concept, PCA-based approach discussed above was compared with two conventional approaches for PRF thermometry. All images were registered to the first image prior to application of all approaches. The first approach is an averaged baseline methodology, where $B_{Ave}$ is used as reference for phase difference. The second approach is a dictionary based methodology, where the best matching baseline image is looked up for each therm image. For all three approaches, the average phase over the SNR-based mask (discussed above with reference to Step 120 of FIG. 1) was removed after baseline correction to eliminate global phase drift. The resultant phase difference images were scaled by $(-\gamma \cdot B \cdot TE \times 0.01 \text{ ppm}/^\circ C.)^{-1}$ to estimate temperature difference relative to the first acquisition. Because the expected temperature change was 0 in absence of external heating, temporal mean ($\mu_T$) and standard deviation ($\sigma_T$) of the estimated ΔT series were used to assess estimation bias and variability.

Figure 2A:
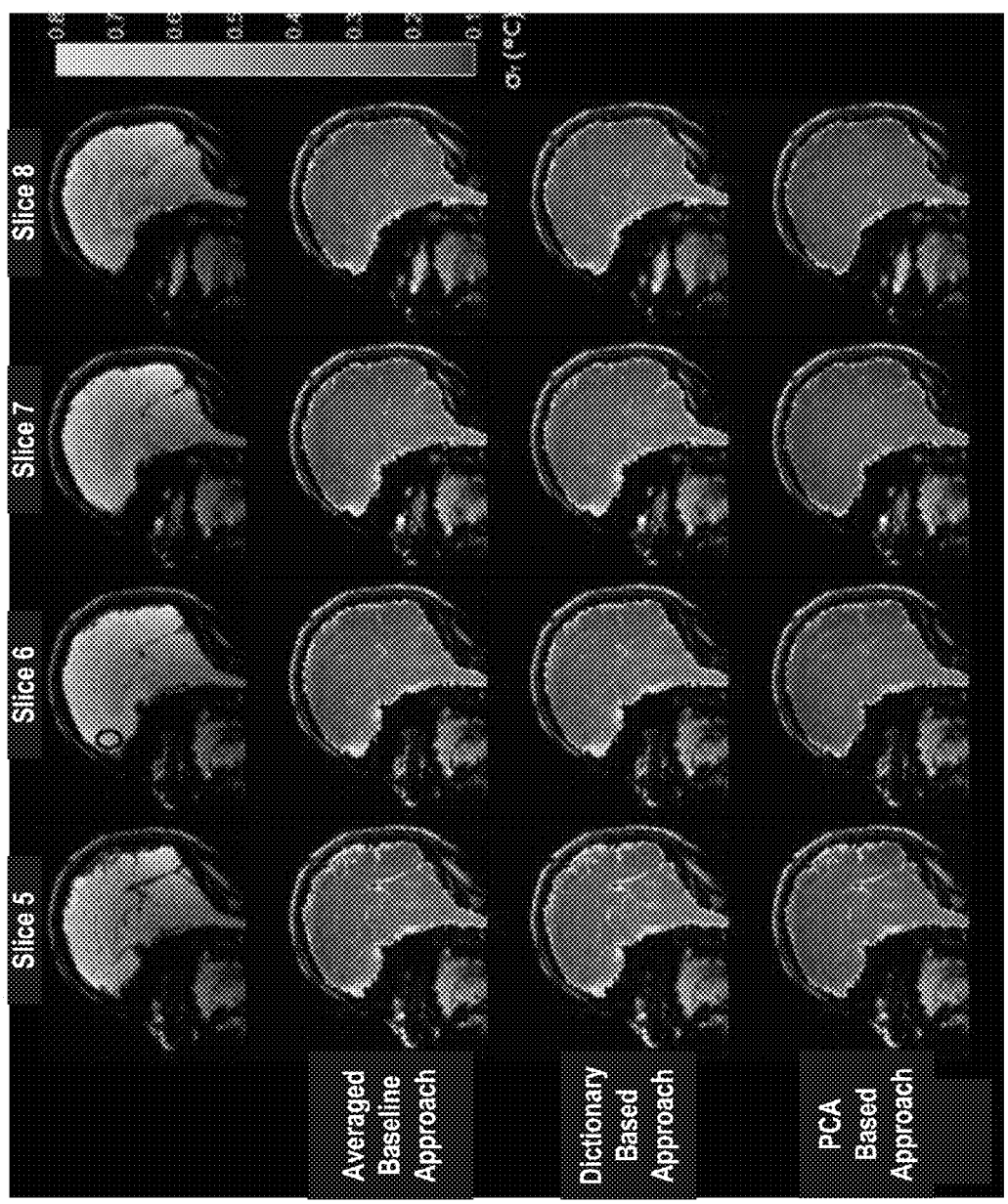
FIG. 2A shows standard deviation maps of an estimated temperature difference series, comparing three different baseline removal schemes.
Figure 2B:
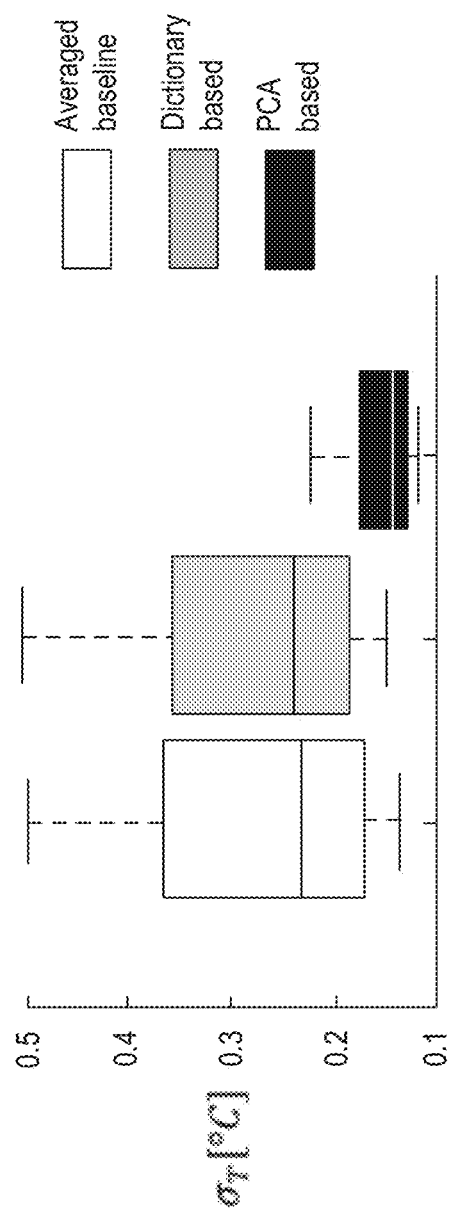
FIG. 2B shows box plots corresponding to the standard deviation of the estimated temperature difference series over a region of interest (ROI) drawn in the frontal cortex, as shown in FIG. 2A (row 1, column 2)

FIGS. 2A and 2B illustrate $\sigma_T$ for different baseline removal schemes. FIG. 2A shows $\sigma_T$ maps for the compared baseline removal techniques are shown in FIG. 2A. A box plot for $\sigma_T$ obtained from a region of interest (ROI) covering the orbitofrontal cortex (indicated on the magnitude image) is shown in FIG. 2B. The PCA-based method described in FIG. 1 results in major reduction in $\sigma_T$ compared with the other approaches.

FIGS. 3A and 3B show $\mu_T$ for different baseline removal schemes. FIG. 3A shows $\mu_T$ maps for the compared baseline removal techniques. FIG. 3B shows a box plot for $\mu_T$ obtained from an ROI a covering the orbitofrontal cortex (indicated on the magnitude image). FIGS. 3A and 3B suggest that PCA based baseline correction results in much smaller bias in areas prone to susceptibility related $B_0$ changes, compared with the other approaches.

FIGS. 4A-4D show a comparison of baseline removal techniques for cardiac thermometry data. The $\sigma_T$ and $\mu_T$ maps for the compared baseline removal techniques are shown in FIGS. 4A and 4B, respectively. Box plots for $\sigma_T$ and $\mu_T$ obtained from an ROI covering the left ventricle are shown in FIGS. 3C and 3D, respectively. The PCA-based method described in FIG. 1 results in major reduction in $\sigma_T$ compared with the other approaches. Also, $\mu_T$ values get closer to 0 when the proposed approach is used for correction.

The PCA-based method described herein outperforms the averaged baseline and dictionary based approaches in the regions prone to motion related $B_0$ changes. This can be attributed to two reasons. First, the PCA bases can be combined to "interpolate" motion states that fall between those captured by the baseline images, and therefore are not exactly represented by any baseline image. Second, PCA bases have reduced noise as compared with individual baseline images, because incoherent noise is pushed to the bases corresponding to smaller eigenvalues.

Figure 5:
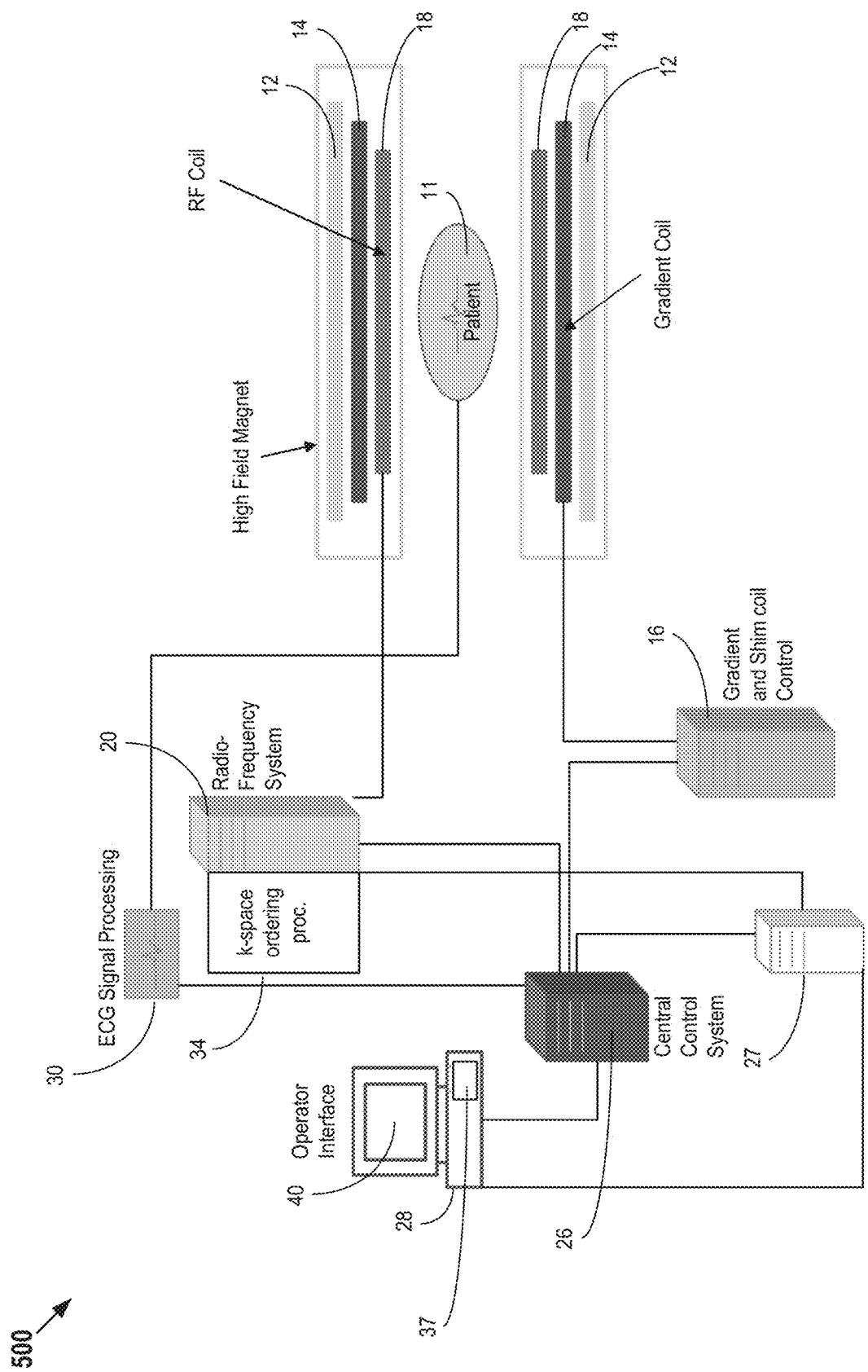
FIG. 5 shows an example MRI system that may be used in acquisition of the reference and dynamic images, according to some embodiments of the present invention.

FIG. 5 shows an example MRI system that may be used in acquisition of the reference and dynamic images, according to some embodiments of the present invention. In system 500, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field and a readout gradient magnetic field that are applied to patient 11.

Further RF (radio frequency) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control computer 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor unit 34 to provide an MR dataset to an image data processor for processing into an image. In some embodiments, the image data processor is located in central control computer 26. However, in other embodiments such as the one depicted in FIG. 5, the image data processor is located in a separate unit 27. Electrocardiogram (ECG) synchronization signal generator 30 provides ECG signals used for pulse sequence and imaging synchronization. A two or three dimensional k-space storage array of individual data elements in k-space component processor unit 34 stores corresponding individual frequency components comprising an MR dataset. The k-space array of individual data elements has a designated center and individual data elements individually have a radius to the designated center.

A magnetic field generator (comprising coils 12, 14 and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components is sequentially acquired during acquisition of an MR dataset representing an MR image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components is substantially minimized.

Central control computer 26 uses information stored in an internal database to process the detected MR signals in a coordinated manner to generate high quality images of a selected slice(s) of the body (e.g., using the image data processor) and adjusts other parameters of system 500. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control computer 26 and enables user modification of magnetic resonance imaging signals in substantially real time. Display processor 37 processes the magnetic resonance signals to provide image representative data for display on display 40, for example.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

The term "computer readable medium" as used herein refers to any medium that participates in providing instructions to the processor for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk or removable media drive. One non-limiting example of volatile media is dynamic memory. Non-limiting examples of transmission media include coaxial cables, copper wire, and fiber optics, including the wires that make up one or more buses. Transmission media may also take the form of acoustic or light waves, such as those generated during radio wave and infrared data communications.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f), unless the element is expressly recited using the phrase "means for."

We claim:

1. A method for phase correction in proton resonance frequency (PRF) thermometry applications, the method comprising:
    acquiring a series of magnetic resonance (MR) images comprising a first MR image and plurality of subsequent MR images depicting an anatomical area of interest, wherein the MR images are acquired while tissue in the anatomical area of interest is undergoing a temperature change;
    registering each subsequent MR image to the first MR image to yield a plurality of registered images;
    computing a plurality of basis images from the registered images using Principal Component Analysis (PCA);
    using the basis images to remove motion-related phase changes from a second series of MR images, thereby yielding a motion corrected second series of MR images; and
    generating one or more temperature difference maps depicting a relative temperature change for the tissue in the anatomical area of interest based on the motion corrected second series.

2. The method of claim 1, wherein the series of MR images are acquired using a 2D or 3D single echo gradient-recalled echo (GRE) sequence.

3. The method of claim 1, wherein the series of MR images are acquired using a 3D segmented echo-planar imaging (EPI) sequence.

4. The method of claim 1, wherein the series of MR images are single shot EPI images with or without navigation.

5. The method of claim 1, wherein the basis images are computed using a process comprising:
   calculating a complex mean of the registered images;
   computing a signal-to-noise ratio (SNR)-based spatial mask on the registered images using the complex mean;
   performing PCA over the spatial mask to yield a plurality of eigen images; and
   retaining a subset of the eigen images as the basis images.

6. The method of claim 5, wherein the eigen images are computed by performing PCA on complex phase difference between the registered images and the complex mean.

7. The method of claim 1, wherein the basis images are used to remove the motion-related phase changes from the second MR images according to a process comprising:
   computing a phase difference between each registered image and a corresponding previous image in the second series of MR images;
   generating the motion corrected second series of MR images by removing a projection of each complex phase difference onto a subspace spanned by the plurality of basis images.

8. A system for phase correction in proton resonance frequency (PRF) thermometry applications, the system comprising:
   a plurality of RF coils configured to acquire a series of magnetic resonance (MR) images comprising a first MR image and plurality of subsequent MR images depicting an anatomical area of interest, wherein the MR images are acquired while tissue in the anatomical area of interest is undergoing a temperature change;
   one or more displays;
   one or more computers connected to the RF coils, wherein the computers are configured to:
      register each subsequent MR image to the first MR image to yield a plurality of registered images;
      compute a plurality of basis images from the registered images using Principal Component Analysis (PCA);
      use the basis images to remove motion-related phase changes from a second series of MR images, thereby yielding a motion corrected second series of MR images; and
      generate one or more temperature difference maps for presentation on the display, wherein the temperature difference maps depict a relative temperature change for the tissue in the anatomical area of interest based on the motion corrected second series.

9. The system of claim 8, wherein the series of MR images are acquired using a 2D or 3D single echo gradient-recalled echo (GRE) sequence.

10. The system of claim 8, wherein the series of MR images are acquired using a 3D segmented echo-planar imaging (EPI) sequence.

11. The system of claim 8, wherein the series of MR images are single shot EPI images with or without navigation.

12. The system of claim 8, wherein the basis images are computed using a process comprising:
   calculating a complex mean of the registered images;
   computing a signal-to-noise ratio (SNR)-based spatial mask on the registered images using the complex mean;
   performing PCA over the spatial mask to yield a plurality of eigen images; and
   retaining a subset of the eigen images as the basis images.

13. The system of claim 12, wherein the eigen images are computed by performing PCA on complex phase difference between the registered images and the complex mean.

14. The system of claim 8, wherein the basis images are used to remove the motion-related phase changes from the second MR images according to a process comprising:
   computing a phase difference between each registered image and a corresponding previous image in the second series of MR images;
   generating the motion corrected second series of MR images by removing a projection of each complex phase difference onto a subspace spanned by the plurality of basis images.

15. An article of manufacture for phase correction in proton resonance frequency (PRF) thermometry applications, the article of manufacture comprising a non-transitory, tangible computer-readable medium holding computer-executable instructions for performing a method comprising:
   receiving a series of magnetic resonance (MR) images comprising a first MR image and plurality of subsequent MR images depicting an anatomical area of interest, wherein the MR images are acquired while tissue in the anatomical area of interest is undergoing a temperature change;
   registering each subsequent MR image to the first MR image to yield a plurality of registered images;
   computing a plurality of basis images from the registered images using Principal Component Analysis (PCA);
   using the basis images to remove motion-related phase changes from a second series of MR images, thereby yielding a motion corrected second series of MR images; and
   generating one or more temperature difference maps depicting a relative temperature change for the tissue in the anatomical area of interest based on the motion corrected second series.

16. The article of manufacture of claim 15, wherein the basis images are computed using a process comprising:
   calculating a complex mean of the registered images;
   computing a signal-to-noise ratio (SNR)-based spatial mask on the registered images using the complex mean;
   performing PCA over the spatial mask to yield a plurality of eigen images; and
   retaining a subset of the eigen images as the basis images.

17. The article of manufacture of claim 16, wherein the eigen images are computed by performing PCA on complex phase difference between the registered images and the complex mean.

18. The article of manufacture of claim 15, wherein the basis images are used to remove the motion-related phase changes from the second MR images according to a process comprising:
   computing a phase difference between each registered image and a corresponding previous image in the second series of MR images;
   generating the motion corrected second series of MR images by removing a projection of each complex phase difference onto a subspace spanned by the plurality of basis images.

* * * * *